United States Patent
Yu et al.

(10) Patent No.: US 8,282,829 B2
(45) Date of Patent: Oct. 9, 2012

(54) SYSTEM AND METHOD FOR AUTOMATED DATA COLLECTION OF TWENTY-FOUR HOUR ULTRAFILTRATION AND OTHER PATIENT PARAMETERS USING WIRED OR WIRELESS TECHNOLOGY

(75) Inventors: Alex Anping Yu, Safety Harbor, FL (US); Robert W. Childers, Trinity, FL (US); Pete Hopping, Luiz, FL (US)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 540 days.

(21) Appl. No.: 12/469,371

(22) Filed: May 20, 2009

(65) Prior Publication Data

US 2010/0298662 A1    Nov. 25, 2010

(51) Int. Cl.
*B01D 61/34* (2006.01)
*B01D 61/32* (2006.01)

(52) U.S. Cl. ............ 210/645; 210/85; 210/86; 210/87; 210/96.2; 210/321.6; 210/646

(58) Field of Classification Search .................. 210/85, 210/87, 96.2, 143, 321.6, 645–647, 86; 604/4.01, 604/5.01, 6.01, 6.09, 29, 65–67; 700/273, 700/282; 713/168
See application file for complete search history.

(56) References Cited

U.S. PATENT DOCUMENTS

| | | | |
|---|---|---|---|
| 4,324,663 A | 4/1982 | Hirel et al. | |
| 4,464,172 A | 8/1984 | Lichtenstein | |
| 4,976,683 A | 12/1990 | Gauthier et al. | |
| 5,151,082 A * | 9/1992 | Gorsuch et al. | 604/5.04 |
| 5,158,538 A | 10/1992 | Shaw | |
| 5,350,357 A | 9/1994 | Kamen et al. | |
| 5,372,147 A | 12/1994 | Lathrop, Jr. et al. | |
| 5,445,610 A | 8/1995 | Evert | |
| 5,555,897 A | 9/1996 | Lathrop, Jr. et al. | |
| 5,558,638 A * | 9/1996 | Evers et al. | 604/66 |
| 5,722,947 A | 3/1998 | Jeppsson et al. | |
| 5,827,820 A | 10/1998 | duMoulin et al. | |
| 5,843,474 A | 12/1998 | Williams | |

(Continued)

FOREIGN PATENT DOCUMENTS

WO    2007/126360    11/2007

OTHER PUBLICATIONS

U.S. Appl. No. 12/131,755, filed Jun. 2, 2008, Lee et al.

(Continued)

*Primary Examiner* — Joseph Drodge
(74) *Attorney, Agent, or Firm* — K&L Gates LLP

(57) ABSTRACT

A dialysis system includes: a dialysis machine for performing a first dialysis session on a patient at a first time of a day; a remote exchange device for performing a second dialysis session on the patient at a second time of the day, the remote exchange device configured to record an amount of ultrafiltration ("UF") that is removed from the patient over the second dialysis session; and a communication link between the dialysis machine and the remote exchange device, wherein the dialysis machine is configured to receive the recorded amount UF removed from the remote exchange device via the communication link and determine a total amount of UF removed from the patient over the first and second sessions.

19 Claims, 9 Drawing Sheets

U.S. PATENT DOCUMENTS

| | | | |
|---|---|---|---|
| 5,902,336 | A | 5/1999 | Mishkin |
| 5,938,634 | A | 8/1999 | Packard |
| 6,074,359 | A | 6/2000 | Keshaviah et al. |
| 6,117,122 | A | 9/2000 | Din et al. |
| 6,232,286 | B1 | 5/2001 | Goodearl et al. |
| 6,234,992 | B1 | 5/2001 | Haight et al. |
| 6,497,676 | B1 | 12/2002 | Childers et al. |
| 6,558,667 | B2 | 5/2003 | Nakanishi |
| 6,585,677 | B2 | 7/2003 | Cowan, Jr. et al. |
| 6,592,542 | B2 | 7/2003 | Childers et al. |
| 6,595,948 | B2 | 7/2003 | Suzuki et al. |
| 6,814,547 | B2 | 11/2004 | Childers et al. |
| 6,932,787 | B2 | 8/2005 | Cowan et al. |
| 6,979,309 | B2 * | 12/2005 | Burbank et al. .............. 604/6.16 |
| 7,033,539 | B2 * | 4/2006 | Krensky et al. .................. 422/44 |
| 7,107,837 | B2 | 9/2006 | Lauman et al. |
| 7,153,286 | B2 | 12/2006 | Busby et al. |
| 7,297,689 | B2 | 11/2007 | Miyata |
| 7,303,541 | B2 | 12/2007 | Hamada et al. |
| 7,354,417 | B1 | 4/2008 | Levin et al. |
| 7,421,316 | B2 | 9/2008 | Gray et al. |
| 7,507,219 | B2 | 3/2009 | Noack |
| 7,507,220 | B2 | 3/2009 | Childers et al. |
| 7,618,392 | B2 | 11/2009 | Martis et al. |
| 2004/0111293 | A1 | 6/2004 | Firanek et al. |
| 2004/0111294 | A1 | 6/2004 | McNally et al. |
| 2004/0220832 | A1 | 11/2004 | Moll et al. |
| 2005/0089994 | A1 | 4/2005 | Neftel |
| 2007/0106247 | A1 | 5/2007 | Burnett et al. |
| 2007/0125709 | A1 * | 6/2007 | Nigam ........................... 210/645 |
| 2008/0097283 | A1 | 4/2008 | Plahey |
| 2008/0183126 | A1 | 7/2008 | Landherr et al. |
| 2008/0183127 | A1 | 7/2008 | Landherr et al. |
| 2008/0243211 | A1 | 10/2008 | Cartwright et al. |
| 2009/0037216 | A1 | 2/2009 | Bluemler et al. |
| 2009/0076856 | A1 | 3/2009 | Darby et al. |
| 2009/0187139 | A1 | 7/2009 | Mastalli et al. |
| 2009/0222119 | A1 | 9/2009 | Plahey et al. |
| 2009/0271119 | A1 | 10/2009 | Hamada et al. |
| 2009/0275881 | A1 | 11/2009 | Lo et al. |
| 2009/0275883 | A1 | 11/2009 | Chapman et al. |
| 2009/0294339 | A1 | 12/2009 | Biewer et al. |
| 2009/0299273 | A1 | 12/2009 | Lee et al. |

OTHER PUBLICATIONS

U.S. Appl. No. 12/170,172, filed Jul. 9, 2009, Yu et al.
U.S. Appl. No. 12/170,184, filed Jul. 9, 2009 Yu et al.
U.S. Appl. No. 12/170,204, filed Jul. 9, 2009, Childers et al.
U.S. Appl. No. 12/170,220, filed Jul. 9, 2009, Yu et al.
U.S. Appl. No. 12/170,230, filed Jul. 9, 2009, Yu et al.
U.S. Appl. No. 12/431,458, filed Apr. 28, 2009, Lo, et al.
U.S. Appl. No. 12/431,479, filed Apr. 28, 2009, Chapman et al.
Rippe B. et al. Computer Simulation of Peritoneal Fluid Transport in CAPD. Kidney International, vol. 40 (1991), pp. 315-325.
Vonesh E. F. and Rippe B., Net fluid absorption under membrane transport models of peritoneal dialysis, Blood Purif 1992; 10:209-226.
International Search Report and Written Opinion for International Application No. PCT/US2010/033516 mailed on Nov. 12, 2010.
International Preliminary Report on Patentability for International Application No. PCT/US2010/033516 mailed on Aug. 25, 2011.

* cited by examiner

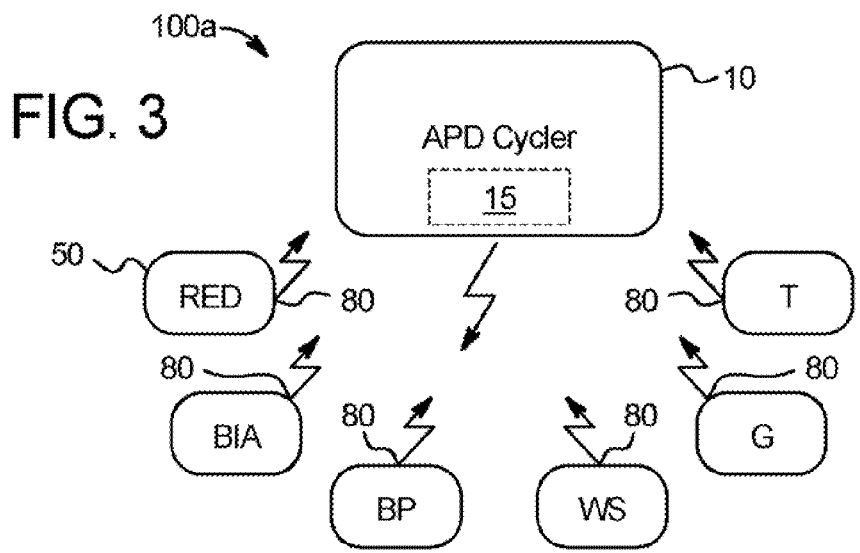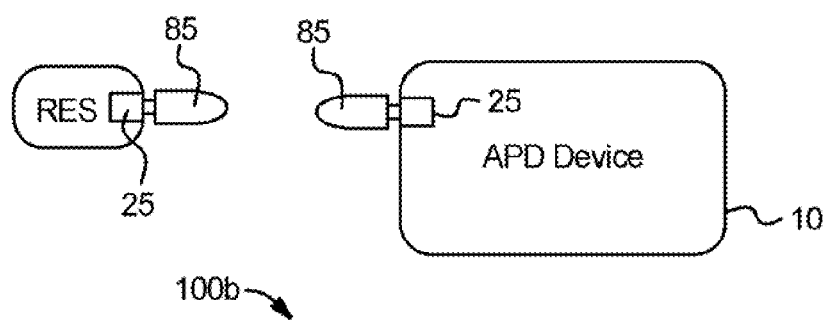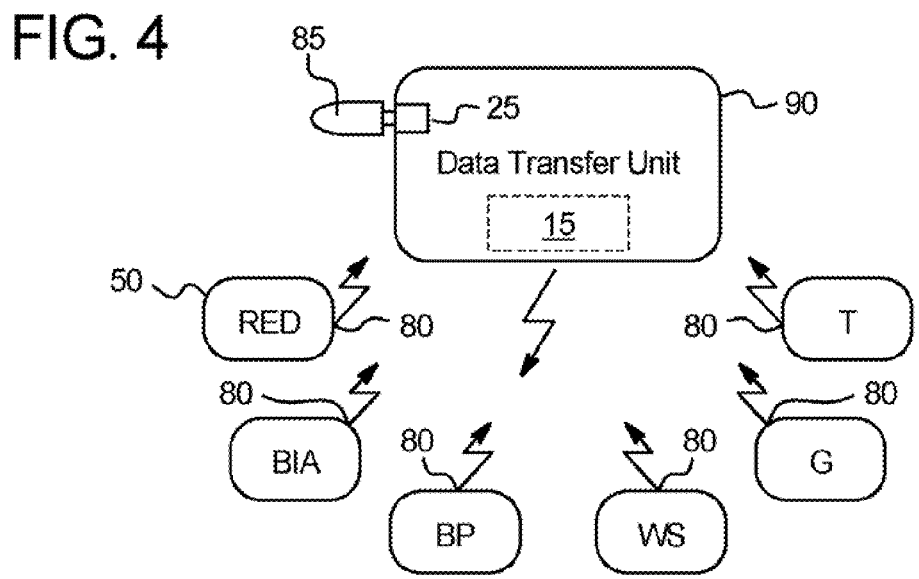

SYSTEM AND METHOD FOR AUTOMATED DATA COLLECTION OF TWENTY-FOUR HOUR ULTRAFILTRATION AND OTHER PATIENT PARAMETERS USING WIRED OR WIRELESS TECHNOLOGY

BACKGROUND

The present disclosure relates to medical fluid delivery and in particular to peritoneal dialysis fluid delivery.

Due to disease or other causes, a person's renal system can fail. In renal failure of any cause, there are several physiological derangements. The balance of water, minerals and the excretion of daily metabolic load is no longer possible in renal failure. During renal failure, toxic end products of nitrogen metabolism (urea, creatinine, uric acid, and others) can accumulate in blood and tissues.

Kidney failure and reduced kidney function have been treated with dialysis. Dialysis removes waste, toxins and excess water from the body that would otherwise have been removed by normal functioning kidneys. Dialysis treatment for replacement of kidney functions is critical to many people because the treatment is life saving. One who has failed kidneys could not continue to live without replacing at least the filtration functions of the kidneys.

One type of dialysis is peritoneal dialysis. Peritoneal dialysis uses a dialysis solution or "dialysate", which is infused into a patient's peritoneal cavity through a catheter implanted in the cavity. The dialysate contacts the patient's peritoneal membrane in the peritoneal cavity. Waste, toxins and excess water pass from the patient's bloodstream through the peritoneal membrane and into the dialysate. The transfer of waste, toxins, and water from the bloodstream into the dialysate occurs due to diffusion and osmosis, i.e., an osmotic gradient occurs across the membrane. The spent dialysate drains from the patient's peritoneal cavity and removes the waste, toxins and excess water from the patient. This cycle is repeated.

There are various types of peritoneal dialysis therapies, including continuous ambulatory peritoneal dialysis ("CAPD") and automated peritoneal dialysis ("APD"). CAPD is a manual dialysis treatment, in which the patient connects an implanted catheter to a drain and allows a spent dialysate fluid to drain from the patient's peritoneal cavity. The patient then connects the catheter to a bag of fresh dialysate and manually infuses fresh dialysate through the catheter and into the patient's peritoneal cavity. The patient disconnects the catheter from the fresh dialysate bag and allows the dialysate to dwell within the cavity to transfer waste, toxins and excess water from the patient's bloodstream to the dialysate solution. After a dwell period, the patient repeats the manual dialysis procedure.

In CAPD the patient performs several drain, fill, and dwell cycles during the day, for example, about four times per day. Each treatment cycle typically takes about an hour. APD is similar to CAPD in that the dialysis treatment includes a drain, fill, and dwell cycle. APD machines, however, perform three to four cycles of peritoneal dialysis treatment automatically, typically overnight while the patient sleeps. Like CAPD, APD machines connect fluidly to an implanted catheter, to one or more sources or bags of fresh dialysate and to a fluid drain.

The APD machines pump fresh dialysate from the dialysate source, through the catheter, into the patient's peritoneal cavity and allow the dialysate to dwell within the cavity so that the transfer of waste, toxins and excess water from the patient's bloodstream to the dialysate solution can take place. The APD machines then pump spent dialysate from the peritoneal cavity, though the catheter, to the drain. APD machines are typically computer controlled so that the dialysis treatment occurs automatically when the patient is connected to the dialysis machine, for example, when the patient sleeps. That is, the APD systems automatically and sequentially pump fluid into the peritoneal cavity, allow for a dwell, pump fluid out of the peritoneal cavity and repeat the procedure. As with the manual process, several drain, fill, and dwell cycles will occur during APD. A "last fill" is typically used at the end of APD, which remains in the peritoneal cavity of the patient when the patient disconnects from the dialysis machine for the day.

Some patients perform a midday exchange away for the APD machine. The patient has to manually keep track of the amount of ultrafiltration ("UF") removed during a midday exchange and then add it to the UF amount removed using the APD machine (typically at night) to arrive at a total daily or twenty-four hour total UF. A need exists for an improvement over this current practice. Further, a need exists for an APD machine to conveniently accept and monitor other patient parameters pertinent to a dialysis therapy, such as blood pressure and patient weight, which can then be used to help obtain a better therapy.

SUMMARY

The present disclosure provides a dialysis system and method for automated twenty-four hour ultrafiltration ("UF") recordation and patient data using wired or wireless technology. The present disclosure is described in connection with peritoneal dialysis ("PD"), however, many concepts set forth herein are applicable to other medical fluid treatments and in particular other types of renal failure therapies, such as hemodialysis ("HD"), hemofiltration ("HF") and hemodiafiltration ("HDF").

In one primary embodiment, the present system and method includes a dialysis machine, such as an automated peritoneal dialysis ("APD") machine and a remote exchange device ("RED"). The APD machine typically runs a night therapy in which the machine beings by drawing spent fluid from the patient's peritoneum and then filling the patient with fresh dialysate. That fresh dialysate dwells within the patient for a period of time (dwell period), absorbing toxins and UF (basically built-up fluid that the patient cannot excrete) until the fresh dialysate becomes spent. The APD machine repeats the above cycle a number of times, such as three to five times, each cycle accumulating additional UF, which the APD machine records.

In addition to the night therapy, many PD patients also perform an additional midday exchange that also removes toxins an UF from the patient. The initial nighttime drain will then be the spent midday fill. The midday exchange is performed using the RED, which also accumulates the amount of UF that the patient produces. In the method and system of the present disclosure, the amount of UF accumulated via the midday exchange is communicated to the APD machine, which totals the UF removed for a full day's or twenty-four hour treatment, removing the burden from the patient from doing so manually.

In one embodiment, the RED is brought into proximity with the APD machine, such that the RED can send information to the machine. The communication can be via a wire that is attached between the RED and the APD machine, such as USB cable or serial cables. Alternatively, the communication is wireless, e.g., via Bluetooth, Zigbee, WiFi, or wireless USB.

In another embodiment, the system includes an intermediate data transfer unit, The RED downloads therapy information to the data transfer unit through wired or wireless communication in a manner the same as or similar to the direct communication embodiment discussed above. The data transfer unit includes a memory storage member port, such as a USB port, which allows the patient to insert a memory storage member, such as a USB flash drive or travel drive, into the port. Pertinent data is then downloaded from the data transfer unit to the storage member, which is then brought to the APD machine. The APD machine is provided with processing and memory for integrating the midday data with the overnight data to arrive at twenty-four hour data, e.g., twenty-four UF removed.

The intermediate data transfer unit is useful when multiple APD machines exist in the system, e.g., for an in-center application. Here, the data transfer unit operates with multiple RED's for different patients. Each patient is provided with his or her own memory storage member or card. The patient downloads data from the RED to the data transfer unit and inserts his/her memory card into the unit. The unit may seek a patient identifier so that it can cue information for multiple patients while waiting to receive a memory card. Upon receiving the identifier, which for example matches an identifier sent from the RED along with therapy data, the appropriate data is downloaded to the patient's data card or member, which the patient can then bring to the APD machine to upload the data into the machine. In an alternative embodiment, the data transfer unit waits until prior data is downloaded from the patient's data card before accepting data from a second machine. Even here, it is desirable to require patient identification so that the system and method can confirm that the data is being downloaded to the appropriate data transfer card.

In a further alternative embodiment the RED is provided with a port for receiving the patient's data card or member. Patient identification may or may not be required for downloading data from the RED to the patient's data card.

The system and method does not require an intermediate data transfer unit to operate with multiple machines, e.g., in a center. The patient's RED can be wired directly to the machine storing the patient's night therapy data. Here, a patient ID code may be required to ensure that the APD machine is being linked to the appropriate RED. When communication is done wirelessly, the system can require one or both of (i) encryption which initiates security features before the wireless link between the APD machine and the RED is completed and (ii) a patient identifier confirming that the RED is linked to the proper machine.

It is contemplated for any of the embodiments discussed herein to provide for the data transfer from peripheral devices different from and in addition to the RED. Communication may wired but is in one preferred embodiment wireless to avoid multiple cables. In addition to the RED, the APD machine can be configured to read any one or more of: (i) bioelectric impedance data (which measures patient fluid hydration status and estimates the patient's dry weight); (ii) blood pressure data (e.g., from a blood pressure cuff); (iii) body weight (e.g., from a weigh scale); (iv) patient blood glucose data (e.g., from a glucometer); and patient body temperature (e.g., from a thermometer). Each of the above devices is modified in one embodiment to be a wireless data master, so that the APD cycler is then a wireless data slave. The result is a wireless network in which any of the master peripheral devices can send information to the APD machine (assuming encryption and/or identifier security measures are met) when the APD machine is visible to others or in a discoverable mode.

It is accordingly an advantage of the present disclosure to provide a method and system for automatically calculating and monitoring twenty-four hour ultrafiltration removed from the patient.

It is another advantage of the present disclosure to provide a method and system that automatically receives multiple patient parameters pertinent to therapy, such as patient weight, blood pressure, glucose level, temperature and bioimpedance hydration data.

It is a further advantage of the present disclosure to provide a system and method that can be expanded to encompass multiple machines, e.g., for in-center use.

It is yet another advantage of the method or system of the present disclosure to use wireless technology in one embodiment for the automatic exchange of data.

Additional features and advantages are described herein, and will be apparent from the following Detailed Description and the figures.

BRIEF DESCRIPTION OF THE FIGURES

FIG. 3 is a schematic view of one embodiment of the system and accompanying method of the present disclosure.

FIG. 4 is a schematic view of a second embodiment of the system and accompanying method of the present disclosure.

DETAILED DESCRIPTION

Dialysis Machine

Figure 1:
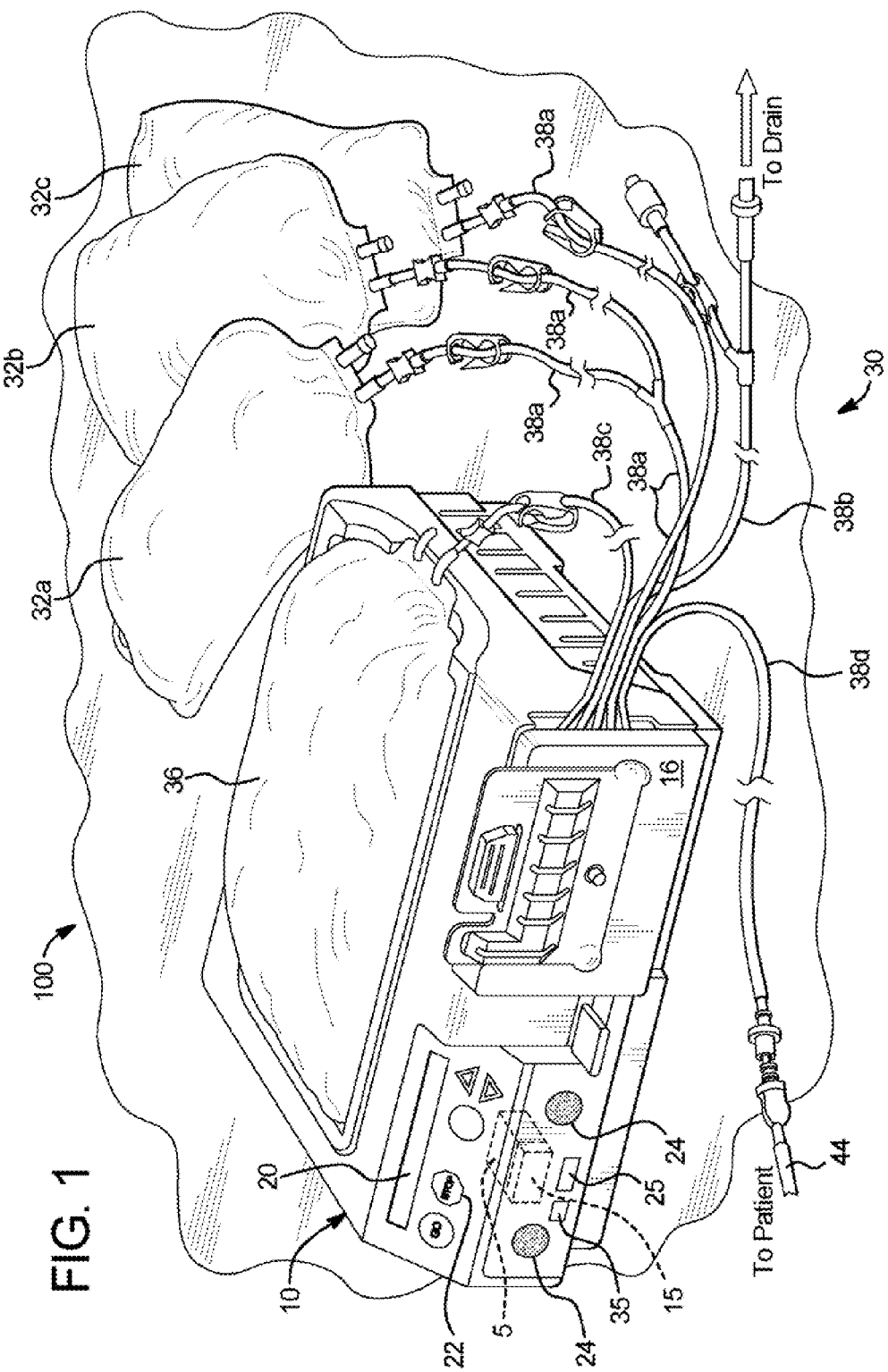
FIG. 1 is a perspective view of one embodiment of an automated peritoneal dialysis machine ("APD"), and in particular a peritoneal dialysis machine used to perform a nighttime dialysis treatment.

Referring now to the drawings and in particular to FIG. 1, a data collection system 100 uses a dialysis machine 10. System 100 is applicable generally to any type of renal failure therapy system, such as peritoneal dialysis ("PD"), hemodialysis ("HD"), hemofiltration ("HF"), hemodiafiltration ("HDF") and continuous renal replacement therapy ("CRRT"). System 100 could also be used outside of the renal field, such as for medication delivery in general and for blood processing. For ease of illustration, however, system 100 is described in general as a dialysis system, and in one particularly well-suited application as a PD system.

Dialysis instrument 10 is configured for whichever type of renal failure therapy system is used. Dialysis instrument 10 includes a central processing unit ("CPU") and a plurality of controllers (e.g., safety, valve, heater, pump, video and audio (e.g., voice guidance) controllers) operable with the CPU. The CPU operates with a graphical user-machine interface ("GUI"), e.g., via the video controller. The GUI includes a video monitor 20 and one or more type of input device 22, such as a touch screen or electromechanical input device (e.g., membrane switch). The CPU also operates with a wireless communicator 15 and/or receives data from a memory device port 25, such as a USB flash drive or travel drive port, discussed in more detail below.

The CPU and video controller in cooperation with video monitor 20 provide UF and other data downloading instructions visually via characters/graphics to the patient or caregiver. For example, characters/graphics can be displayed to provide instructions regarding when to attempt to send data wirelessly to machine 10 or where on machine 10 to plug a flash drive for data downloading. Additionally or alternatively, The CPU and voice guidance controller in cooperation with speakers 24 provide audible instructions via voice guidance to the patient or caregiver. For example, voice guidance can be given to provide instructions regarding the downloading of data from a remote exchange device ("RED") 50 (FIG. 2) to machine 10.

As seen in FIG. 1, dialysis instrument 10 accepts and operates with a disposable apparatus 30. Disposable apparatus 30 includes one or more supply bag 32a to 32c (referred to herein collectively as supply bags 32 or individually, generally as supply bag 32). While three supply bags 32 are shown, system 10 can employ any suitable number of supply bags. Disposable set 30 also includes a drain bag (not illustrated), a warmer bag 36, bag tubes 38a to 38d (referred to herein collectively as tubing or tubes 38 or individually, generally as tube 38) and a disposable pumping/valve cassette (not illustrated).

Depending on the type and structure of machine 10, one or more of the items of disposable apparatus 30 may not be needed. For example, machine 10 can pump spent fluid to a house drain, such as a bathtub, a toilet or sink, instead of to a drain bag. Machine 10 can also include an inline heater, in which case warmer bag 36 is not needed.

As mentioned, a disposable cassette (located behind door 16 of machine 10 in FIG. 1) connects to supply bags 32, a drain bag and warmer bag 36 via tubes 38a, 38b and 38c, respectively. Tube 38d runs from the cassette to a patient connection 44. The cassette in one embodiment includes a rigid structure having (i) rigid outer walls, (ii) a base wall from which inner pump chambers, valve chambers and inner fluid pathways extend, (iii) rigid fluid ports that connect sealingly to tubing 38, and (iv) a pair of flexible membranes or sheets sealed to outer rigid walls and possibly, additionally to inner rigid walls. Tubing 38 can be fixed to a port, such that bags 32 are spiked for fluid connection. Alternatively, tubing 38 is fixed to bags 32 and the cassette ports are spiked for fluid connection.

Machine 10 can actuate the pump and valve chambers of the cassette pneumatically, mechanically or both. The illustrated embodiment uses pneumatic actuation. The HomeChoice® APD system marketed by the assignee of the present disclosure uses a pneumatic system described in U.S. Pat. No. 5,350,357 ("The '357 Patent"), the entire contents of which are incorporated herein by reference. Here, machine 10 includes a membrane gasket, which creates different sealed areas with cassette sheeting at each of the pump and valve chambers of the cassette. Machine 10 in the illustrated embodiment includes a door 16, which closes against the cassette. Door 16 includes a press plate (not illustrated), which can be operated mechanically (e.g., via the closing of the door) and/or pneumatically (e.g., via an inflatable bladder located in the door behind the press plate). Pressing the plate against the cassette in turn presses the cassette against the membrane gasket that cooperates with the sheeting of the cassette to pump fluid and open and close valves.

U.S. Pat. No. 6,814,547 ("the '547 patent") assigned to the assignee of the present disclosure, discloses a pumping mechanism in connection with FIGS. 17A and 17B, incorporated herein by reference, which uses a combination of pneumatic and mechanical actuation. FIGS. 15, 16A and 16B of the '547 Patent, incorporated herein by reference, teach the use of mechanically actuated valves. Either or both the '547 pumping mechanism or valves could be used alternatively with machine 10.

Remote Exchange Device ("RED")

Figure 2:
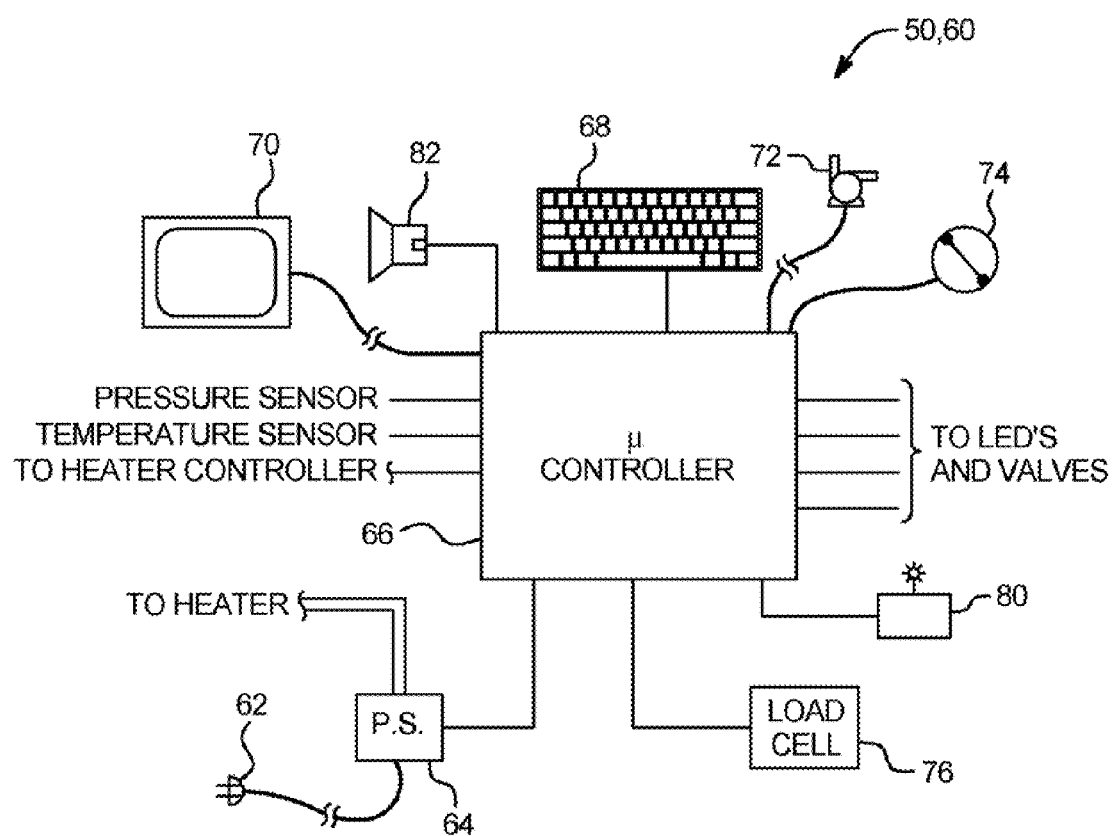
FIG. 2 is a schematic view of one embodiment of a remote exchange device ("RED") used to perform a midday exchange for the patient.

One suitable embodiment for a remote exchange device ("RED") 50 is described in U.S. patent application Ser. No. 12/131,755 ("the '755 Application"), filed Jun. 2, 2008, entitled "Remote Exchange Peritoneal Dialysis", the entire contents of which are incorporated herein directly by reference. The control scheme for the incorporated device is illustrated here in FIG. 2, which is adapted from FIG. 2 of the '755 Application. FIG. 2 depicts a control system for a flexible, portable RED 50. The control system receives conventional electrical power from a power cord 62 that is suitable for normal household, clinic, or hospital AC power. The principal user of power in this system is the heater. Thus, the input power is sent to a power supply 64 for conversion into the particular power needed for the heater, as shown. The power supply also produces 5 VDC power for the system microcontroller 66 and the other components of the system as needed, such as for the LED lamps. Other voltages may be produced by the power supply 64 as needed for each component of the system. The microcontroller receives a number of inputs from system components, such as a temperature selector, and, if used, an input and output to a separate heater controller. The microcontroller 66 may itself include a routine for controlling the heater rather than using a separate heater controller. A temperature sensing element, or temperature sensor, such as a thermocouple or thermistor, is used to measure the temperature of the dialysis fluid and to control the heating of the dialysis fluid. A pressure sensor may also be placed at one or more points within the system to gauge pressure of fluid to and from the patient. In particular, a vacuum gauge, or absolute pressure gage, may be placed on the drain line to avoid using too much suction on the drain line, which could irritate the peritoneum of the patient.

The control system also accepts inputs from a load cell 76 of RED 50 and from a keypad 68, or optionally, a keyboard. The control system also includes a number of outputs. A monitor 70, such as a video screen or a digital read-out, may be used to output the temperature of the dialysate, the time elapsed, and so forth. Other outputs include signals to vacuum pump 72 or dialysate pump 74, which may be a peristaltic pump, membrane pump or other desired pump. The system also includes signal processing circuitry and a wireless communicator 80. The signal processing circuitry of control system 60 and wireless communicator 80 are small and compact and fit well within control system of RED 50.

One suitable wireless module for communicator 80 is Zig-Bee/IEEE 805.15.4. This is a standard for a very low power radio system with a very limited range, about 10 to 20 feet. Modules made in accordance with this standard may be purchased from Maxstream, Inc., Lindon, Utah, U.S.A., Helicomm, Inc., Carlsbad, Calif., U.S.A., and ANT, Cochrane, Alberta, Canada. The module is very small, and may be about 2 cm square (about 1 inch square), and about 3 mm thick (⅛ inch). The signal processing circuitry formats the digital data and routes it to a data buffer before transmission to a remote site. Other equipment in accord with other specifications may be used instead, such as IEEE 802.15.1 ("Bluetooth"). Alternatively, the microprocessor may report desired therapy information via a landline, such as a wire harness connected to the appropriate site for receiving the information, such as a communications center of a hospital or clinic.

The system may sound an alarm if therapy parameters are exceeded through speaker 82 or by illuminating one or more LED on RED 50. An alarm may also be given through the monitor 70 in conjunction with stopping the therapy session. The controller may use the outputs by sending a signal to the appropriate output when the temperature of the warmed dialysate fluid is too high or too low, when the therapy session has taken too long, or when any other required parameter is exceeded.

Data Transfer From RED 50 And Other Peripherals to APD machine 10

APD machine 100 records ultrafiltrate ("UF") removed for night exchanges automatically. Until now, however, the patient had to manually weigh the day exchange fill volume and drain volume by scale and manually enter these values into the APD machine. Referring to FIG. 3, system 100a automates the data collection of UF and other values, which includes both night and midday exchange values. System 100a adds the night exchange UF and midday exchange UF to arrive at the total daily UF. System 100a (and the other systems herein) allow the midday exchanges to be performed away from the patient's home and without using APD machine 10.

RED 50 provides the midday exchange and the capability of recording fill volume and drain volume to calculate UF for one or more midday exchange. The RED 50 uses wireless communicator 80 to communicate with wireless communicator 15 of APD machine 10. Wireless communicator 80 has a transmit function and alternatively additionally has receiving functionality for receiving information, e.g., from APD machine 10. Wireless communicator 15 of APD machine 10 has receive functionality and alternatively additionally has transmit functionality for send data, e.g., to RED 50.

It is contemplated with system 100a that the patient return home, e.g., from work, and place RED 50 within the communication range of wireless communicators 15 and 80. When both APD machine 10 and RED 50 are then powered, the UF data is downloaded from RED 50 to APD machine 10. The downloading can be automatic or require a user input from either input devices 22 of machine 10 or via keyboard 68 of RED 50. Appropriate information regarding the downloading of UF data, such as the fill volume amount, the drain volume amount and the resulting UF can be displayed on one or both of video monitor 20 of machine 10 and monitor 70 of RED 50. The calculation of UF removed for the midday exchange (total midday drain volume less total midday fill volume) may be performed via microcontroller 60 of RED 50 or via the CPU of machine 10. The overall daily or twenty-four hour UF removed (nightly total UF and total midday UF) is performed at the CPU of machine 10 in one embodiment. In this manner, better therapy, e.g., PD therapy is provided because critical data is recorded, transferred and manipulated automatically, removing recording and calculating errors and making the therapy easier for the patient.

FIG. 3 shows that APD 10 can accept other data wirelessly and is not limited to just receiving midday exchange UF data remotely from RED 50. For example, APD cycler 10 may additionally receive bioelectric impedance analysis data from ("BIA") wirelessly from a BIA device fitted with a wireless communicator, such as communicator 80. APD cycler 10 can receive blood pressure ("BP") data wirelessly from a blood pressure or monitor fitted with a wireless communicator, such as communicator 80. The same hold true for patient weight via a weight scale ("WS"), glucose data ("G") from a glucometer or patient temperature data ("T") from a thermometer, each fitted with a wireless communicator, such as communicator 80.

APD machine 10, in general, uses each of the various UF, BIA, WS, BP, G and T data to evaluate an ongoing or completed therapy. The machine may receive any desired one or combination of UF, BIA, WS, BP, G and T data. Moreover, the different data does not have to each come from a separate device. For example a single unit measuring BIA, T, G and possibly BP could be used with RED 50 for UF and a separate weigh scale for WS. Or, such a device could be combined with RED 50.

In an alternative embodiment, any of the RED 50, BIA, BP, WS, G and T devices can communicate via wired communication with APD machine 10. Here, machine 10 and the associated device each accept a wire, e.g., for serial or USB communication.

Referring now to FIG. 4, system 100b illustrates an alternative system that employs an intermediate data transfer unit ("DTU") 90. DTU 90 receives any one or more of UF, DIA, BP, WS, G and T data wired or wirelessly via the apparatus and methodology described herein. DTU 90 also has a port 25 for accepting a memory device 85, e.g., a USB serial drive or flash drive, which plugs into port 25. Information sent wirelessly to DTU 90 is transferred onto drive 85 which is then plugged into memory port 25 at APD machine 10. APD machine 10 then retrieves the data from memory device 85.

FIG. 4 shows another alternative way that UF data can be transferred from RED 50 to APD machine 10. Here, RED 50 is also provided with a memory device port 25 that can accept a memory device 85 to obtain the midday exchange UF data. The memory device 85 is then brought to APD machine 10 and plugged into port 25 of machine 10 to download the UF information into the machine.

Figure 5:
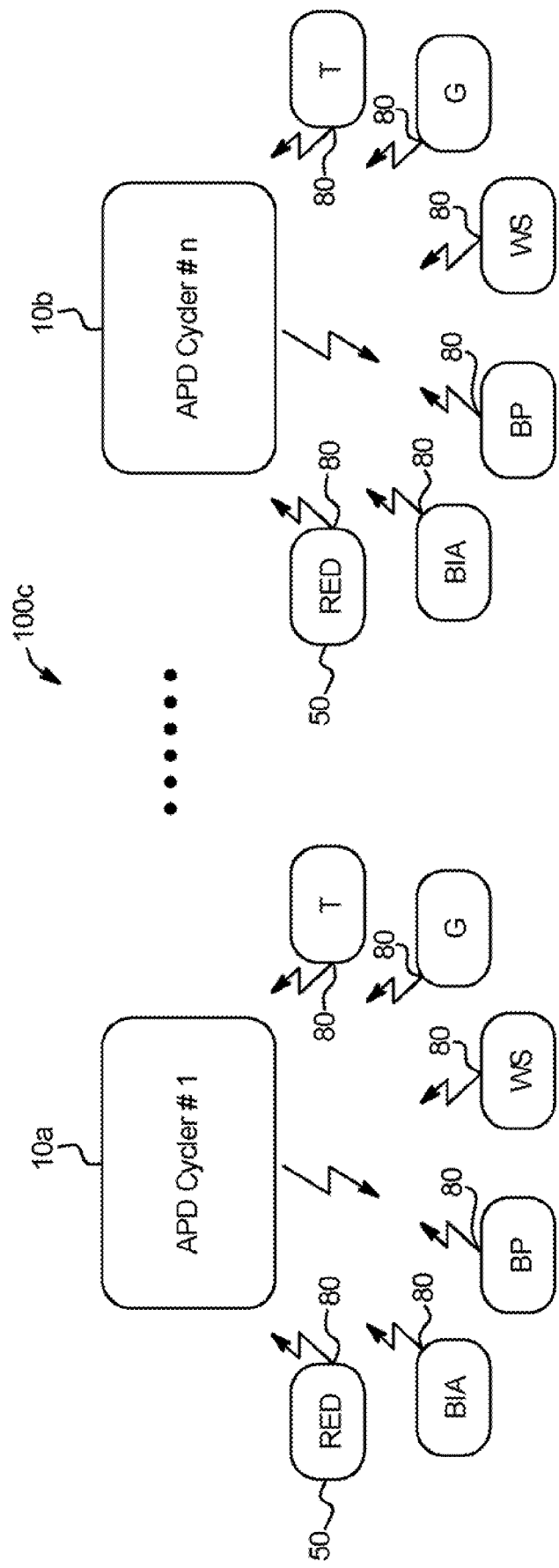
FIG. 5 is a schematic view of a third embodiment of the system and accompanying method of the present disclosure.
Figure 6:
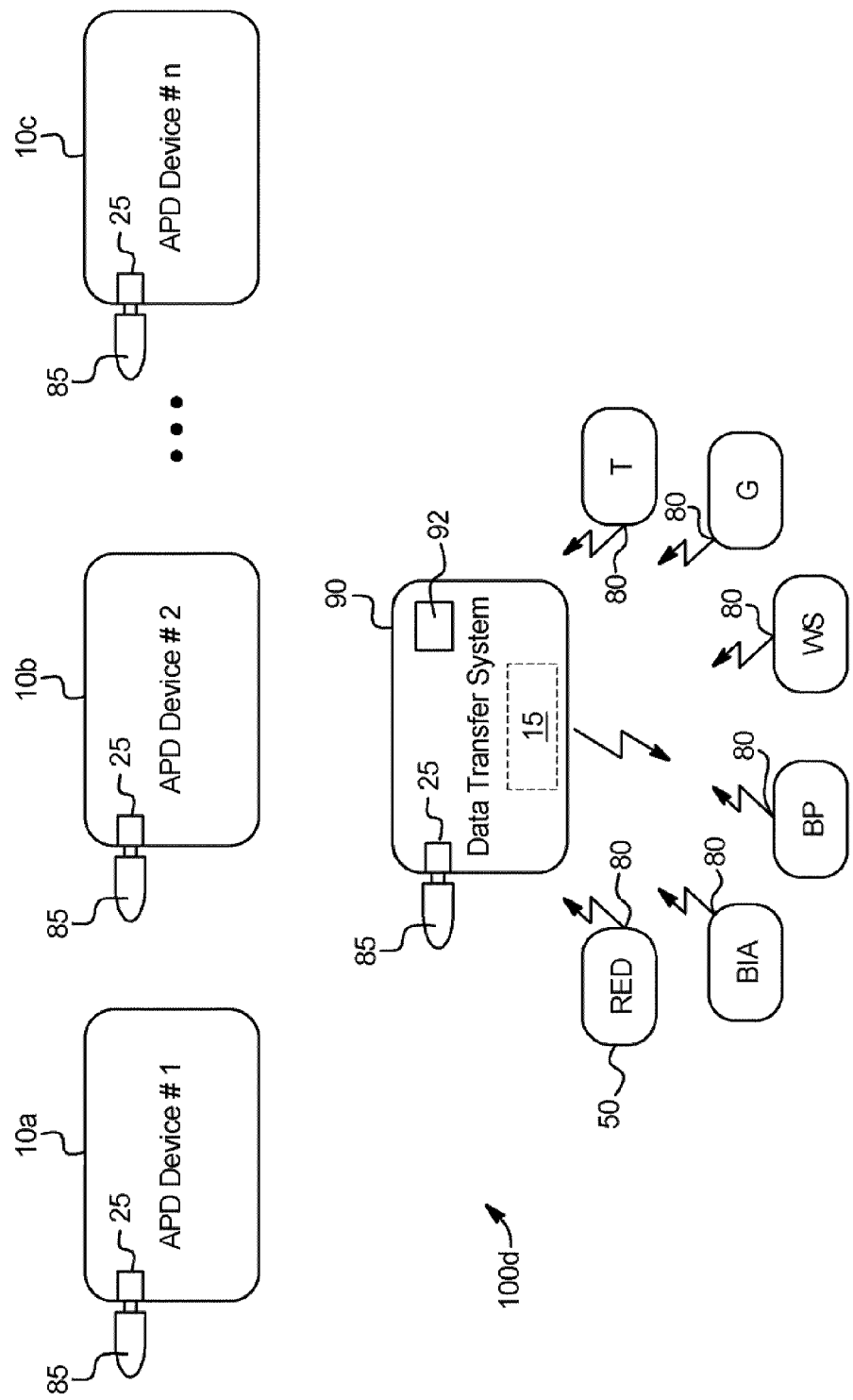
FIG. 6 is a schematic view of a fourth embodiment of the system and accompanying method of the present disclosure.

FIGS. 5 and 6 illustrate systems 100c and 100d, respectively that are used when multiple APD machines are located in the same environment, e.g., multiple machines in a center. In a dialysis center or hospital, it is possible that multiple APD machines 10 treat multiple patients at the same time. System 100c of FIG. 5 illustrates machines 10a and 10b, each of which has its own RED 50, BIA, BP, WS, G and T devices, which communicate wireless or via wired communication with APD machine 10*a* or 10*b*. Described below are encryption and security technologies that prevent cross-talk between the peripheral devices communicating wirelessly with the appropriate APD machine 10.

FIG. 6 illustrates three APD machines 10*a* to 10*c*. Here, DTU 90 described above is used again. Each machine has its own memory device 85. DTU 90 sequentially receives data from one or more of RED 50, BIA, BP, WS, G and T devices for one patient, transfers the information to the patient's memory device 85, which is then taken to the appropriate APD machine 10*a* to 10*c*. DTU 90 then receives data for the next patient and so on. DTU 90 can require a user name and password to enable data received to be downloaded to a memory device 85. In an embodiment, DTU 90 includes an input device 92 that when pressed cleans the memory within DTU 90 and enables the memory to then accept new data for any one or more of the UF, BIA, BP, WS, G and T data for a new patient. It should be appreciated that system 100*d* of FIG. 6 eliminates the cross-talking issues of system 100*a* of FIG. 5.

Bluetooth wireless technology is one preferred technology and has three range classes shown below in Table 1. Classes I and II may be more suitable for the disclosed operations.

| Class | Maximum Permitted Power | Range (Approximate) |
| --- | --- | --- |
| Class I | 100 mW | ~100 meters |
| Class II | 2.5 mW | ~10 meters |
| Class III | 1.0 mW | ~1 meters |

Bluetooth data rate are shown below in Table 2. System 100 (including all system 100*a* to 100*d*) can use either version 1.2 or 2.0.

| Bluetooth Version | Date Rate |
| --- | --- |
| Version 1.2 | 1 Mbps |
| Version 2.0 | 3 Mbps |

In any of the embodiments described herein, when wireless communication is used, a network may be formed and used. For example, if Bluetooth wireless technology is used, a star topology can be established between APD machine 10 and the peripheral device, such as RED 50. In the resulting piconet, the peripheral device operates as the master, while the APD machine 10 operates as a delegate device. When the patient wants to download data to APD machine 10, the APD machine makes itself "visible to others". That is, APD machine 10 places itself in a discoverable mode in which it may be "discovered" or communicated to by any of the master peripheral devices, such as RED 50, BIA, BP, WS, G and T devices.

It is contemplated that any of the RED 50, BIA, BP, WS, G and T devices will de-power themselves once they have communicated their data to APD machine 10. If any of the devices are battery powered, e.g., BIA, BP, WS, G and T devices, the de-powering will save battery charge.

Figure 7:
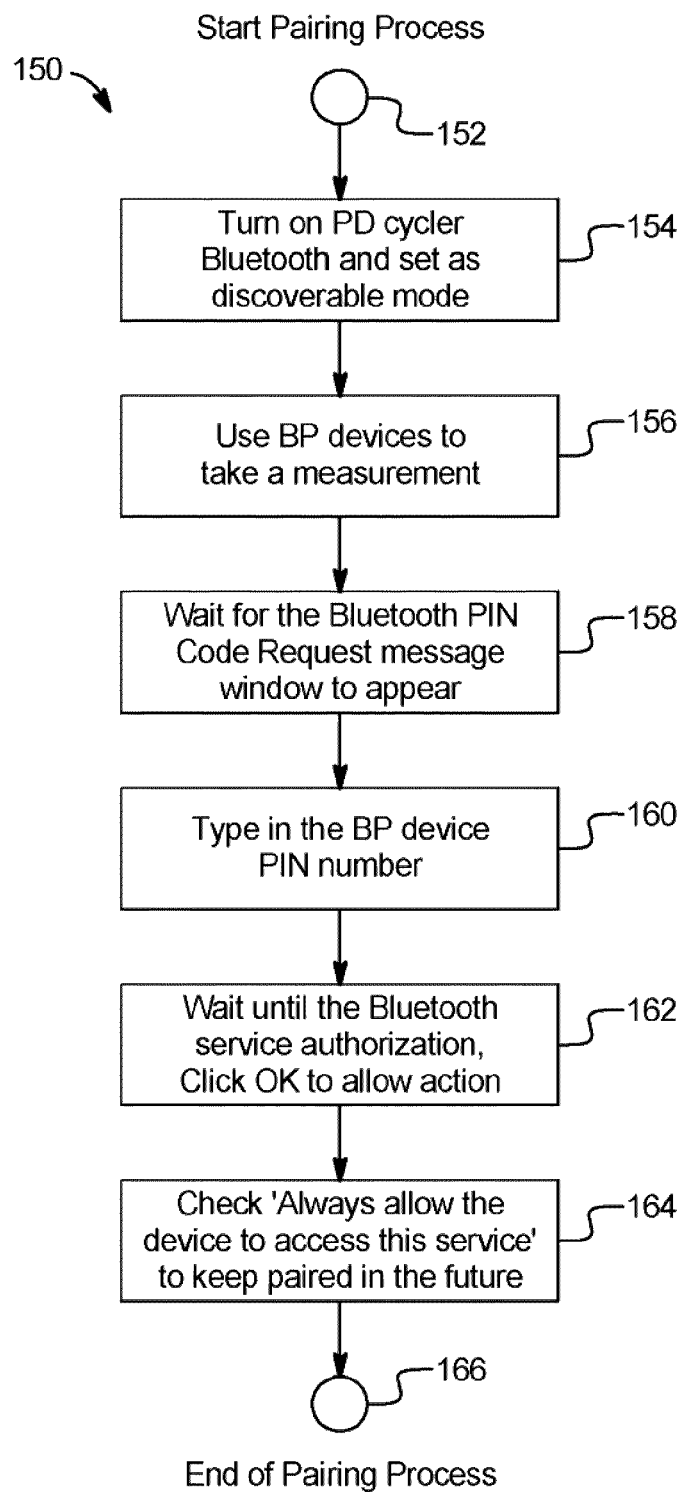
FIG. 7 is a logic flow diagram illustrating one method for pairing a peripheral parameter sensing device with an APD machine.

Referring to FIG. 7, method 150, illustrates one possible way in which one of the peripheral devices becomes paired, or enabled for communication, with an APD machine 10. Method 150 uses BP as an example but applies equally to the other types of peripheral devices. Once pairing is completed, APD machine 10 stores the peripheral device address and corresponding patient identification number ("PIN") into its non-volatile memory. Likewise, the peripheral, e.g., BP, device stores the APD machine 10's wireless or Bluetooth address into its non-volatile memory. In this manner, the pairing process only has to be performed once for the APD machine and any particular peripheral device.

At circle 152, the pairing sequence 150 begins. At block 154, APD machine 10 is powered and set in wireless discoverable mode to be "visible to others". At block 156, the patient uses the BP device to take a blood-pressure measurement. At block 158, method 150 waits until a wireless or Bluetooth PIN code request appears in video monitor 20 of APD machine 10 (or on computer linked to APD machine). At block 160, the patient or caregiver enters the BP PIN into the CPU of APD machine 10 via input device 22 or a computer linked to APD machine 10. At block 162, method 150 waits for authorization for the wireless or Bluetooth service. This authentication in general, entails confirmation of a unique Bluetooth Wireless device address (e.g., a forty-eight bit address unique to the world), and user entering the security PIN. The APD device could also require verification of patient ID or name.

The patient or the caregiver then presses OK or confirms to allow further action. At block 164, the patient or caregiver selects an option to keep the APD machine 10 and the BP device paired in the future. This may entail checking "always allow the device to access this service" on a computer screen linked to APD machine or on video monitor 20 of APD machine 10.

Patient security is a priority for system 100. It is important that APD machine 10 receives the correct data for a particular patient. It is also important that others can not access the patient's data without authorization. Regarding this latter concern, it is contemplated to use propriety protocols for communication between the peripheral devices and APD machine 10. The protocols require that the machine maintain customized software to be able to receive and process information from the peripheral devices. The software prevents a third party who may have the PIN and Bluetooth address of the APD machine 10 from intercepting the patient's information being sent from the remote device.

The wireless technology, e.g., Bluetooth, can operate in the following security modes

| | |
| --- | --- |
| Security mode 1: | No authentication or encryption |
| Security mode 2: | No security initiated at Bluetooth link, or link establishment. Instead security is enforced at connection level (e.g. SDP, RFCOMM) establishment. |
| Security mode 3: | Initiate security procedures before the link setup is complete. Two different security policies are possible: always demand authentication or always demand both authentication and encryption. |

The inventors recommend security mode three for communication between any of RED 50, BIA, BP, WS, T and G devices and the APD machine. Authentication involves the PIN and addresses described above. The encryption involves: (i) unique wireless device number and security PIN number (built in the original purchased Bluetooth wireless blood pressure and weight scale device); (ii) 64, 128, 192 or 256 bit encryption (the original purchased Bluetooth wireless blood pressure and weight scale devices from A&D has a 128 bit encryption); and (iii) proprietary communication protocol. As shown below, prototype was successfully developed using the proprietary communication protocol and blood pressure and weight scale data were transferred to the target devices.

Generally, the prototype software to interface the wireless peripheral devices was built to interface PC (Windows XP) and HP IPAQ PDA (Model HX2795, using Windows Mobile ). The inventors developed the prototype to interface with wireless weight scale and blood pressure devices provided by A & D Medical, San Jose, Calif. The prototype has been run in Windows XP using a laptop computer or Windows Mobile 5.0 using HP iPAQ PDA. The A & D Medical Bluetooth BP and WS use link-level security and 128 bit encryption. The prototype development tools and hardware in the example prototype software included:

Software Tools:
(i) Visual Studio 2005 Professional with Compact Framework 2.0; and
(ii) Windows Mobile 5.0 SDK installed on top on the Compact Framework.

Hardware Tools:
(i) A&D Medical Blood Pressure Cuff;
(ii) A&D Medical Weight Scale;
(iii) Bluetooth enabled System (e.g., HP Compaq nc6220 with Bluetooth feature);
(iv) Bluetooth Dongle (Kinsington, Bluetooth 2.0, potential linking of up to seven devices within a sixty-five foot range); and
(v) HP iPAQ, Model HX2795b, Processor ARM920T PXA27x, Microsoft Windows Mobile Version 5.0.

The Bluetooth prototype application was developed on Visual Studio 2005 platform using C# (C Sharp) programming language. The A&D medical devices follow the Bluetooth Serial Port Profile, so once the connection is established, the data is sent as in the serial port emulation.

After the BP or WS reading is taken, the device looks for Bluetooth discoverable computers/PDA's (e.g., machine 10) and starts the inquiry procedure. A standard PIN is stored in the peripheral device. Once the PIN request is obtained, the user responds by inputting the correct pin number, and the wireless connection is created. After the pairing process is completed, the peripheral BP and WS devices store the address of the machine 10 access point to which it is connected for the next reading. Data in the future is then transferred to the stored machine 10 access point's address by default.

Microsoft NET Framework 2.0 has a built-in Serial Port class. The Serial port class can be used to open the Port in which the data is received. The data received is decoded and displayed. The software prototype works above the layers of Bluetooth architecture, on the high level application layer connected to the emulated serial port.

Figure 8:
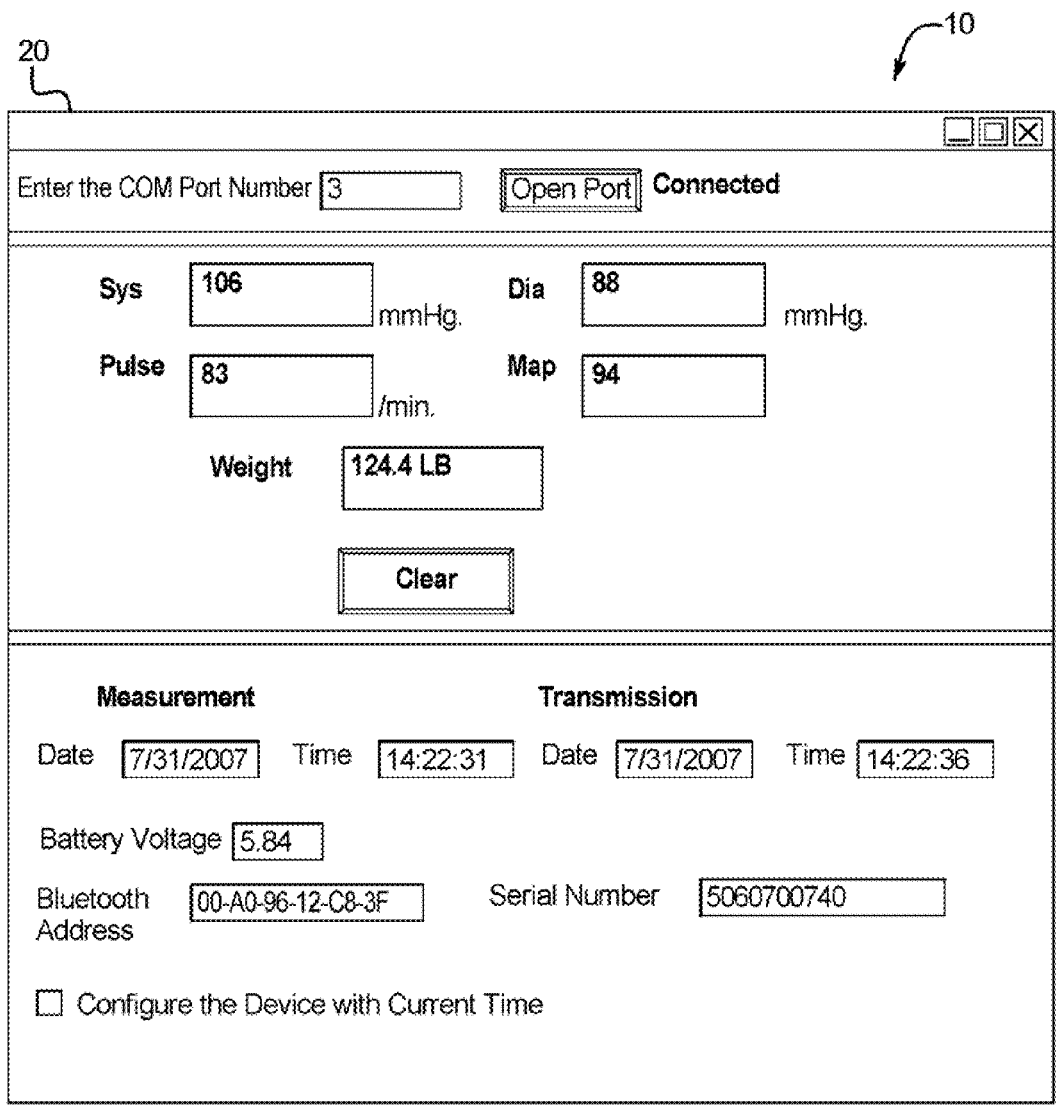
FIG. 8 is a sample display screen of an embodiment of the APD machine of the present disclosure, showing weight and blood pressure read wirelessly from peripheral devices.

A first prototype application software was developed for the Windows XP environment. This first prototype software required the user to input the computer's or machine 10's serial port number, which is used for communication. Once a reading is taken, the peripheral device (e.g., BP cuff or the weight scale) looks for the stored access point address and transmits the data when the address is found. The computer or machine 10 port is opened at the application end and receives the data, which unpacks the data and sends an acknowledgement back to the peripheral BP or WS device. FIG. 8 shows an example screen that the prototype software displayed. The screen shows information such as the measurement date and time, transmission date and time, device address, serial number. There is also an option to calibrate a clock located inside the peripheral device, e.g., the A&D Bluetooth peripheral device (e.g., BP cuff or WS) having a communication protocol using a configuration packet that allows the PIN to be changed and the clock to be synchronized. The clock includes the year, month, day, hour, minute, and second.

The first prototype used the Windows Mobile 5.0 SDK software, which provides a compact operating system combined with a suite of basic applications for mobile devices based on the Microsoft Win32 application programming interface ("API"). The Microsoft applications programming interface provides functions, libraries, communication protocols, classes and data structures to support building custom applications. Devices that run Windows Mobile™ software include, for example, pocket PCs, smart phones, and portable media centers. Windows Mobile™ software is somewhat similar to the desktop versions of Windows.

Windows CE™ software, also used in the original prototype software, is Microsoft's real-time embedded operating system, which is used for a wide variety of small-footprint devices, including industrial controllers, communications hubs, point-of-sale terminal, and consumer electronics. The Windows Mobile™ platform is built on top of Windows CE™ software and concentrates on lower-level operating system ("OS") specifics, such as the kernel, memory management, driver architecture, etc.

The original prototype software also used a Visual Studio 2005 platform provided with emulators, which resembles a Windows Mobile 5.0 device. The prototype Software has been tested on the Windows Mobile 5.0 Pocket PC emulator. Since serial ports are used, the serial port of the emulator is mapped to listen to the computer's or machine 10's communications port, upon which the computer or machine listens. In the Configure option of the Emulator, the Serial Port 0 was mapped to the appropriate port number.

Figure 9:
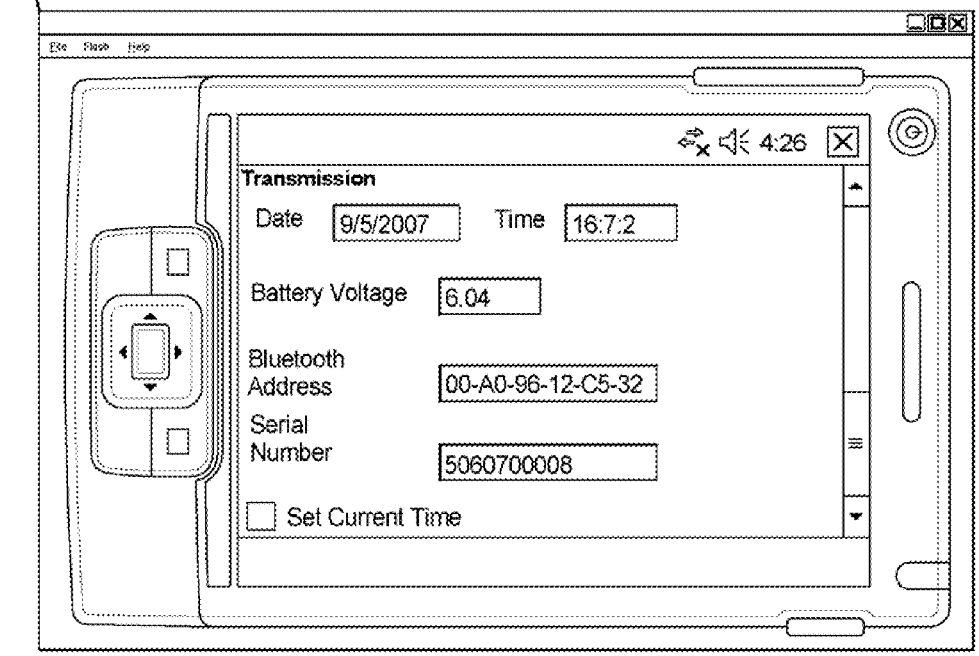
FIG. 9 is a sample display screen of an embodiment of the APD machine of the present disclosure, showing weight scale supply battery voltage, its Bluetooth Address and Serial Number read wirelessly from a weight scale.

FIG. 9 illustrates a screen capture showing the weight scale internal battery voltage, Bluetooth address and the serial number of the weight scale. All of this data has been sent wirelessly from a weight scale to a computer or a machine 10.

Figure 10:
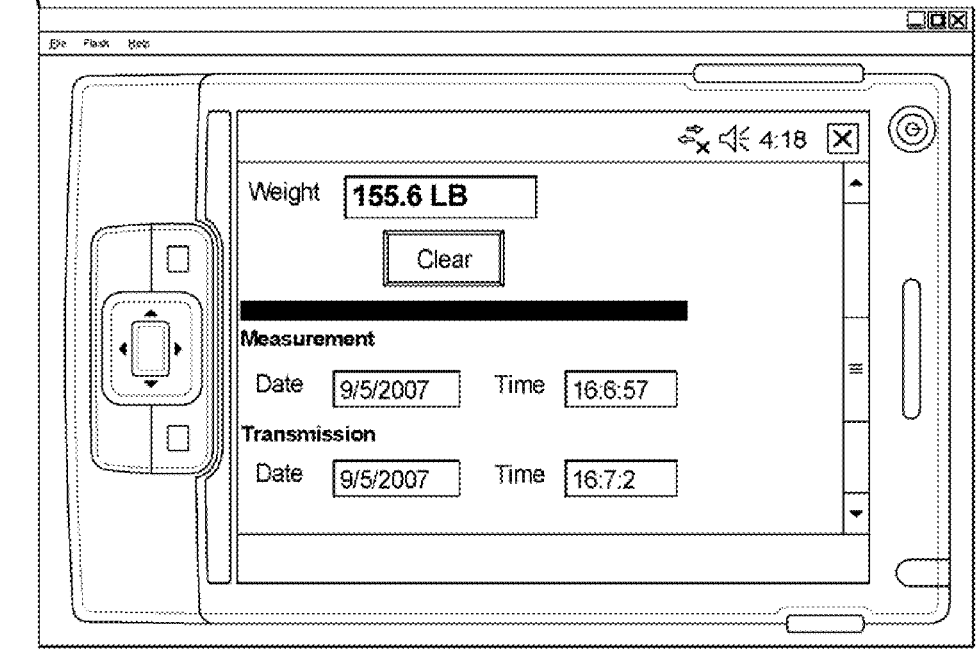
FIG. 10 is a sample display screen of an embodiment of the APD machine of the present disclosure, showing patient weight, peripheral weight scale measurement date and time read wirelessly from a weight scale.

FIG. 10 illustrates a screen capture showing body weight results, measurement date and time, and the transmission date time. All of this data has been sent wirelessly from a weight scale to a computer or a machine 10.

Figure 11:
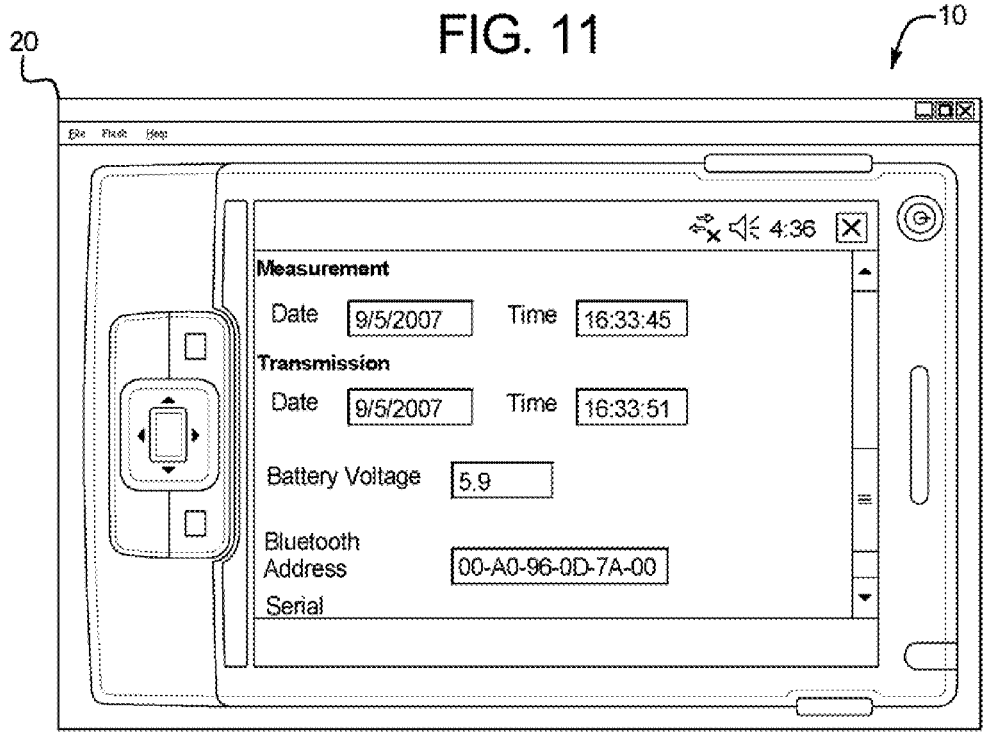
FIG. 11 is a sample display screen of an embodiment of the APD machine of the present disclosure, showing blood pressure cuff supply battery voltage, and its Bluetooth Address read wirelessly from a pressure cuff.

FIG. 11 illustrates a screen capture showing the blood pressure measurement date and time, transmission date time, internal battery voltage, Bluetooth address and the serial number. This information is transmitted by a peripheral blood pressure device together with pressures and pulse rate to a computer or a machine 10.

Figure 12:
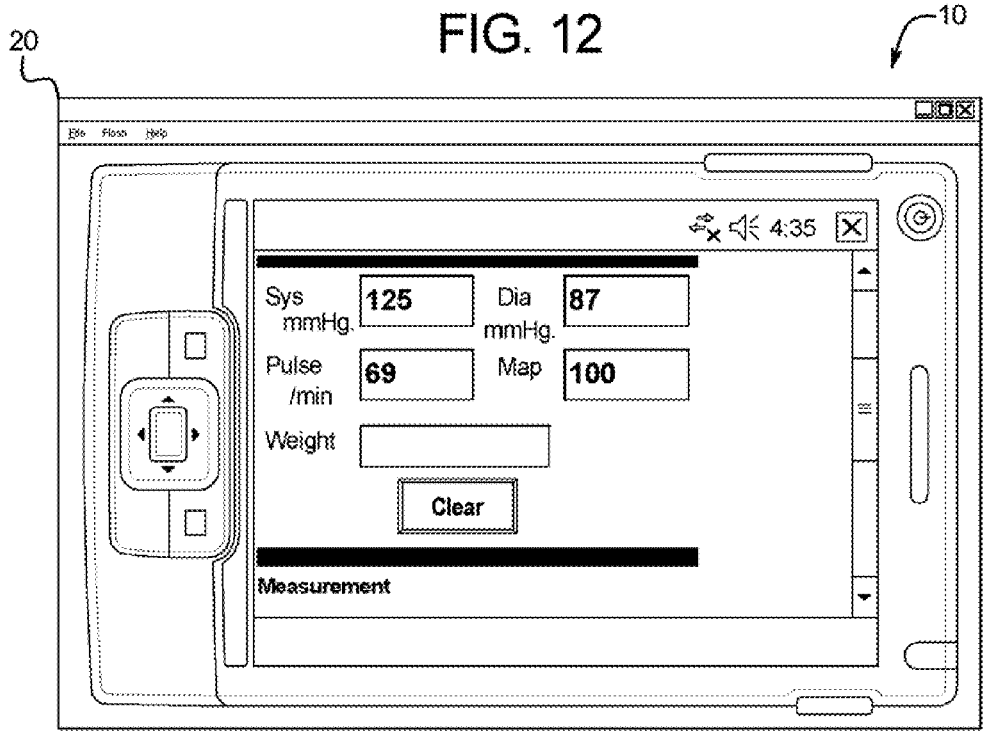
FIG. 12 is a sample display screen of an embodiment of the APD machine of the present disclosure, showing patient systolic and dialystolic blood pressure, pulse rate and mean arterial pressure ("MAP") read wirelessly from a pressure cuff.

FIG. 12 illustrates a screen capture showing prototype results for a blood pressure measurement: e.g., systolic blood pressure, diastolic blood pressure, pulse rate, and mean arterial pressure ("MAP"). All of this data has been sent wirelessly from a the blood pressure device or cuff to a computer or a machine 10.

In an alternative embodiment, the application is run using a personal digital assistant. ("PDA"), which in turn communicates wirelessly or via wired communication with machine 10. In the prototype, the PDA could simulate either APD machine 10 or an actual PDA that a clinician uses in a dialysis center. Many current PDA's have Bluetooth wireless communication capability allowing the custom prototype application to be loaded inside the PDA, allowing the modified PDA prototype to communicate wirelessly with the wireless peripheral devices after pairing. The peripheral devices are again paired using the PIN procedure. The application that is created for the emulator is installed on to the PDA. One process for creating PDA application software for interfacing dialysis machine 10 and one or more peripheral device wirelessly is as follows:

(i) add a project and choose Smart Device CAM project in Microsoft Visual Studio;
(ii) after the project is created, in the project design (in the project explorer, the user can choose design view or class view, for prototype, choose design view) view under the applications folder, right click and choose 'Add Primary output' and choose the 'Application project';
(iii) to create a shortcut from the Start menu, Right click on 'File System on Target Machine' and choose 'Add Special Folder' and under that choose Start Menu folder;
(iv) right click the 'Start Menu folder' and 'Add Project Output' the same way, right click on the 'Primary Output' and choose the first option 'Create Shortcut . . . ', after which a shortcut is created and a suitable shortcut name can be defined;
(v) once the Project is built, a CAB file is created under the /bin/debug folder;
(vi) the mobile device is synched to the computer or machine 10, and the CAB file is stored in the Device's file system; and
(vii) double click on the CAB file in PDA and the application will be installed.

The Bluetooth prototype application software for Windows XP in PC and Windows Mobile 5.0 in PDA has been successfully developed and tested. The conclusions and recommendations for the prototype are listed as follows:
(i) Wireless peripheral devices, such as the A&D weight scale and blood pressure cuff, can be successfully paired with a Bluetooth enabled PDA/PC, especially if the Bluetooth environment is quiet.
(ii) Data transfer has been accomplished successfully in both a quiet and noisy Bluetooth environment once paired with the target PDA/PC (machine 10).
(iii) In a noisy Bluetooth environment (e.g., other Bluetooth devices such as a cell phone, GPS receiver, laptop PC, other A&D scales are on and in active range), the weight scale and BP cuff have attempted to pair with the first available device, which sometimes has not been the intended machine 10 or PDA. This effect is likely the result of the weight scale and BP cuff being the "master" device in the Bluetooth Piconet instead of the "delegate" device. If PDA/PC (machine 10) had instead been configured as the "master", the machine could have searched for and picked desired, specific devices to create a Bluetooth pairing. The peripheral instruments when configured to be the "master" communicator are thus best paired with machine 10 in a "quiet" Bluetooth environment.
(iv) The peripheral devices have been able to successfully transfer data over distance of approximately eighty feet. Transmission distance has been found to be dependent on the transmission medium between the two devices. Moving around a corner or placing an obstruction to wireless transmissions in the path between the peripheral devices and machine 10 have been found to hamper successful data transmission.
(v) During initial pairing, the target instrument 10 can be set to be discoverable and allow all peripheral Bluetooth devices to communicate the instrument. After pairing, it may helpful to set instrument 10 to only communicate with paired devices.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A dialysis system comprising:
a dialysis machine for performing a first dialysis session on a patient at a first time of a day at a first location;
a remote dialysis fluid exchange device for performing a second dialysis session on the patient at a second time of the day at a second location remote from the dialysis machine, the remote exchange device configured to record an amount of ultrafiltration ("UF") that is removed from the patient over the second dialysis session; and
a communication link between the dialysis machine and the remote exchange device,
wherein the dialysis machine is configured to receive the recorded amount of UF removed from the remote dialysis fluid exchange device at the first location via the communication link and determine a total amount of UF removed from the patient over the first and second sessions.

2. The dialysis system of claim 1, wherein the communication link is wired or wireless.

3. The dialysis system of claim 1, wherein the dialysis machine is configured to record an amount of UF that is removed from the patient over the first dialysis session and add that amount to the amount of UF removed over the second dialysis session to determine the total amount of UF removed.

4. The dialysis system of claim 1, wherein the first dialysis session is a nighttime treatment and the second dialysis session is a day exchange.

5. The dialysis system of claim 1, wherein the communication link includes an intermediate data transfer unit, which is configured to receive the recorded amount of UF removed from the remote dialysis fluid exchange device.

6. The dialysis system of claim 5, wherein the intermediate data transfer unit and the remote dialysis fluid exchange device communicate (i) wirelessly or (ii) over a wire.

7. The dialysis system of claim 5, wherein at least one of: (i) the dialysis machine and the intermediate data transfer unit each include a memory storage member port, the memory storage member enabling the dialysis machine to receive the recorded amount of UF from the remote dialysis fluid exchange device; (ii) the dialysis machine and the intermediate data transfer unit are configured to communicate wirelessly so that the dialysis machine can receive the recorded amount of UF from the remote dialysis fluid exchange device; and (iii) the dialysis machine and the intermediate data transfer unit are configured to communicate via a wire so that the dialysis machine can receive the recorded amount of UF from the remote dialysis fluid exchange device.

8. The dialysis system of claim 5, wherein the intermediate data transfer unit is further configured to receive, for communication to the dialysis machine, at least one of: (i) blood pressure data, (ii) bioimpedance data, (iii) patient weight data, (iv) patient glucose level data, and (v) patient temperature data.

9. The dialysis system of claim 8, wherein at least one of: (i) each of the different data is sent from a different apparatus corresponding to the particular data and (ii) each of the different data is sent to the intermediate data transfer unit wirelessly.

10. The dialysis system of claim 8, wherein the dialysis machine is a first dialysis machine, and which includes a second dialysis machine in communication with the intermediate data transfer unit for receiving the at least one data.

11. The dialysis system of claim 1, wherein the dialysis machine is further configured to receive at least one of: (i) blood pressure data, (ii) bioimpedance data, (iii) patient weight data, (iv) patient glucose level data, and (v) patient temperature data.

12. The dialysis system of claim 11, wherein at least one of: (i) each of the different data is sent from a different apparatus corresponding to the particular data and (ii) each of the different data is sent to the dialysis machine wirelessly.

13. The dialysis system of claim 11, the dialysis machine a first dialysis machine, and which includes a second dialysis machine configured to receive the at least one data from a separate source than that for the first dialysis machine.

14. The dialysis system of claim 13, wherein at least one of the: (i) dialysis machines and (ii) the separate sources are at least one of (a) encrypted and (b) provided with an authentication number for secure wireless communication.

15. A dialysis method comprising:
accumulating a first amount of ultrafiltration ("UF") removed from a patient over a nighttime therapy automatically via a dialysis machine at a first location;
recording a second amount of UF removed from the patient over a day time exchange automatically via a remote dialysis fluid exchange device at a second location;
sending the second amount of UF removed electronically to the dialysis machine at the first location; and
at the first location, summing the first and second UF amounts to arrive at a total UF amount removed from the patient for a twenty-four hour period.

16. The method of claim 15, the location being the dialysis machine, and which includes enabling the remote dialysis fluid exchange device after making the recording to be moved within a proximity of the dialysis machine such that the second amount can be sent electronically to the dialysis machine.

17. The method of claim 15, wherein accumulating the first amount of UF removed includes accumulating UF over multiple fill, dwell and drain cycles.

18. The dialysis system of claim 1, wherein the first location is at a home of the patient, and the second location is away from the home of the patient.

19. The method of claim 15, wherein the first location is at a home of the patient, and the second location is away from the home of the patient.

* * * * *